United States Patent
Souza et al.

(10) Patent No.: US 11,377,456 B2
(45) Date of Patent: Jul. 5, 2022

(54) CRYSTALLINE FORM OF REMDESIVIR

(71) Applicant: Apotex Inc., Toronto (CA)

(72) Inventors: Fabio E. S. Souza, Mississauga (CA);
Alexander J. Stirk, Cambridge (CA);
Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 17/601,493

(22) PCT Filed: May 25, 2021

(86) PCT No.: PCT/CA2021/050702
§ 371 (c)(1),
(2) Date: Oct. 5, 2021

(87) PCT Pub. No.: WO2021/248229
PCT Pub. Date: Dec. 16, 2021

(65) Prior Publication Data
US 2022/0144866 A1    May 12, 2022

Related U.S. Application Data

(60) Provisional application No. 63/037,728, filed on Jun. 11, 2020.

(51) Int. Cl.
| | | |
|---|---|---|
| C07F 9/6561 | (2006.01) | |
| C07H 13/12 | (2006.01) | |
| C07H 7/06 | (2006.01) | |
| A61P 31/14 | (2006.01) | |
| A61P 31/12 | (2006.01) | |

(52) U.S. Cl.
CPC ............ *C07F 9/6561* (2013.01); *A61P 31/12* (2018.01); *A61P 31/14* (2018.01); *C07H 7/06* (2013.01); *C07H 13/12* (2013.01); *C07B 2200/13* (2013.01)

(58) Field of Classification Search
None
See application file for complete search history.

(56) References Cited

U.S. PATENT DOCUMENTS

| | | |
|---|---|---|
| 7,301,024 B2 | 11/2007 | Amir et al. |
| 10,065,958 B2 | 9/2018 | Mackman et al. |
| 10,251,904 B2 | 4/2019 | Clarke et al. |
| 10,675,296 B2 | 6/2020 | Larson |
| 10,836,787 B2 * | 11/2020 | Brak ................. C07F 9/6561 |

FOREIGN PATENT DOCUMENTS

| | | |
|---|---|---|
| CN | 113633617 A | 11/2021 |
| WO | 2004054583 A1 | 7/2004 |
| WO | 2012012776 A1 | 1/2012 |
| WO | 2017049060 A1 | 3/2017 |
| WO | 2018204198 A1 | 11/2018 |
| WO | 2019014247 A1 | 1/2019 |

OTHER PUBLICATIONS

Akers, "Chapter 41: Parenteral Preparations", Remington: The Science and Practice of Pharmacy, 21st Edition, 2006, pp. 802-836, Lippincott Williams & Wilkins.
Bernstein, "Is This Material Polymorphic?", Polymorphism in Molecular Crystals, 2002, pp. 9-10, Oxford University Press Inc., New York.
De Savi et al., "Quest for a COVID-19 Cure by Repurposing Small-Molecule Drugs: Mechanism of Action, Clinical Development, Synthesis at Scale, and Outlook for Supply", Org. Process Res. Dev., 2020, pp. 940-976, vol. 24.
Macrae et al., "Mercury CSD 2.0—new features for the visualization and investigation of crystal structures", J. Appl. Cryst, 2008, pp. 466-470, vol. 41.
Parsons et al., "Use of intensity quotients and differences in absolute structure refinement", Acta Cryst., 2013, pp. 249-259, vol. B69.
Sekharan et al., "Selecting a stable solid form of remdesivir using microcrystal electron diffraction and crystal structure prediction", RSC Adv., 2021, pp. 17408-17412, vol. 11.
Sharma et al., "Ultrasound-Assisted Anti-Solvent Crystallization of Telmisartan Using Dimethyl Sulfoxide as Organic Solvent", Crystal Research and Technology, 2018, pp. 1-9, vol. 53.
Sheldrick, "Crystal structure refinement with SHELXL", Acta Cryst., 2015, pp. 3-8, vol. C71.
Sheldrick, "SHELXT—Integrated space-group and crystal-structure determination", Acta Cryst., 2015, pp. 3-8, vol. A71.
"Summary on compassionate use: Remdesivir Gilead", European Medicines Agency, 2020, pp. 1-45.
Thirumalai Rajan, "Complete Specification: Solid state form of (S)-2-ethylbutyl 2-(((S)-(((2R,3S,4R,5R)-5-4-aminopyrrolo[2,1-f][1,2,4]triazin-7-yl)-5-cyano-3,4-dihydroxytetrahydrofuran-2-yl)methoxy)(phenoxy)phosphoryl)amino) propanoate and process for its preparation thereof", MSN Laboratories Privaie Limited, R&D Center, May 2020, pp. 1-22. [English translation of IN 202041021427].

* cited by examiner

*Primary Examiner* — Traviss C McIntosh, III
(74) *Attorney, Agent, or Firm* — The Webb Law Firm

(57) ABSTRACT

The present invention provides a novel crystalline form of remdesivir, remdesivir Form APO-I, including remdesivir and dimethyl sulfoxide, compositions and processes for the preparation thereof, the use of this crystalline form in the treatment of a viral infection, and methods of treating viral infections using the same, and in particular, a viral infection caused by Severe Acute Respiratory Syndrome coronavirus 2 (SARS-CoV-2).

21 Claims, 4 Drawing Sheets

CRYSTALLINE FORM OF REMDESIVIR

CROSS-REFERENCE TO RELATED APPLICATIONS

This application is the United States national phase of International Application No. PCT/CA2021/050702 filed May 25, 2021, and claims priority to U.S. Provisional Patent Application No. 63/037,728 filed Jun. 11, 2020, the disclosures of which are hereby incorporated by reference in their entirety.

BACKGROUND OF THE INVENTION

Field of the Invention

The present invention is directed to novel crystalline forms of Remdesivir, pharmaceutical compositions containing these forms, processes for their preparation, their use in the treatment of viral infections, and methods of treating viral infections.

Description of Related Art

Remdesivir (1), or (S)-2-ethylbutyl-2-(((S)-(((2R,3S,4R,5R)-5-(4-aminopyrrolo[2,1-f][1,2,4]triazin-7-yl)-5-cyano-3,4-dihydroxytetrahydrofuran-2-yl) methoxy)(phenoxy)phosphoryl)amino)propanoate, is a nucleotide analog that is reported to exhibit antiviral properties against Arenaviridae, Coronaviridae, Filoviridae, and Paramyxoviridae viruses. Remdesivir is the active ingredient in VEKLURY® indicated for adults and some pediatric patients for the treatment of coronavirus disease 2019 (COVID-19) requiring hospitalization.

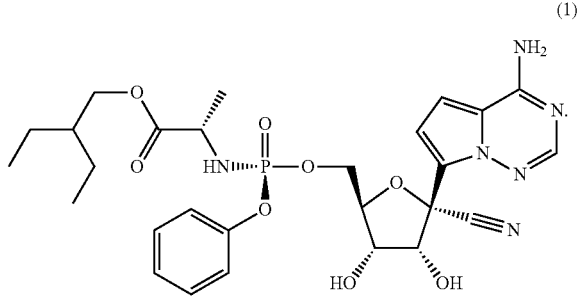 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

(1)

Crystalline forms of remdesivir, including hydrated and solvated forms thereof, are reported in WO 2018/204198 A1. For example, WO 2018/204198 A1 discloses crystalline Forms I to IV and mixtures of Forms II and IV.

According to the European CHMP Summary on Compassionate Use for Remdesivir Gilead (EMEA/H/K/5622/CU), the drug substance remdesivir is manufactured as Form II or mixtures of Form II and another crystalline form. According to the CHMP summary, remdesivir is administered to patients intravenously. However, due to the limited aqueous solubility of remdesivir, which comprises the Form II crystalline form, the beta-cyclodextrin derivative Betadex sulfobutyl ether sodium (SBECD) must be used as a solubilizing agent in the formulation. Poor oral bioavailability of the known form(s) of remdesivir requires intravenous administration, which raises concerns about limits to widespread distribution of the medication to the broader public, if it is shown to be safe and effective in the treatment of COVID-19. Additionally, WO 2019/014247 A1 discloses that remdesivir is chemically unstable in an aqueous environment.

Different crystalline forms of the same compound may have different crystal packing, thermodynamic, spectroscopic, kinetic, surface and mechanical properties. For example, different crystalline forms may have different stability properties such that a particular crystalline form may be less sensitive to heat, relative humidity (RH) and/or light. Different crystalline forms of a compound may also be more susceptible to moisture uptake, resulting in a potential alteration of physical characteristics of the form such as flowability, density or compressibility, which can lead to problems during formulation/tabletting and/or to changes in dissolution rate of the formulated drug product.

For example, unintended absorption of moisture by a hygroscopic crystalline form of a drug substance can alter its resilience to micronization procedures used to enhance solubilization of the drug substance. A particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Particular crystalline forms may also have different solubilities, thereby providing different pharmacokinetic parameters, which allow for specific crystalline forms to be used in order to achieve specific pharmacokinetic targets. Crystalline forms which incorporate a co-former molecule such as solvates may be imparted with properties arising from novel interactions between the compound and the co-former such as differences in permeability or solubility. Differences in solubility between crystalline forms are particularly relevant for compounds exhibiting low solubility, such as remdesivir, where even a modest increase in solubility can provide a beneficial enhancement in bioavailability. A significant increase in the solubility or permeability of a drug such as remdesivir, which exhibits poor oral bioavailability, could be a factor in the provision of an oral formulation.

Although general approaches to crystalline form screening of active pharmaceutical ingredients are known, it is well established that the prediction of whether any given compound will exhibit polymorphism is not possible. Accordingly, it is not possible to extend generalities to the number and kinds of crystalline forms that can exist for remdesivir, or to what methods will be suitable for the preparation of any given crystalline form. Furthermore, prediction of the properties of any unknown crystalline forms, and how they will differ from other crystalline forms of the same compound, remains elusive (Joel Bernstein, *Polymorphism in Molecular Crystals*, Oxford University Press, New York, 2002, page 9).

Owing to the reported low solubility, poor aqueous chemical stability, and dosage form limitations associated with the known forms of remdesivir, there exists a need for novel crystalline forms of remdesivir having improved properties for use in providing drug products containing remdesivir, and commercially amenable processes for their manufacture. Furthermore, the urgency surrounding the development and widespread deployment of effective treatment options for COVID-19 cannot be overstated.

SUMMARY OF THE INVENTION

The remdesivir crystalline form of the present invention comprises remdesivir that has crystallized with dimethyl sulfoxide in the same crystal lattice. Dimethyl sulfoxide has an established safety record and can therefore safely be used in materials intended for use in the preparation of pharmaceutical compositions for administration to humans or animals.

The present invention provides a crystalline form of remdesivir that can be prepared by an efficient and industrially compatible process.

Accordingly, in a first aspect of the present invention, there is provided a crystalline form of remdesivir comprising remdesivir and dimethyl sulfoxide. Preferably, in the crystalline form of the first aspect, the molar ratio of remdesivir to dimethyl sulfoxide is between approximately 1:0.75 and approximately 1:1.25. More preferably, the molar ratio of remdesivir to dimethyl sulfoxide in the crystalline form of the first aspect is approximately 1:1.

In a second aspect of the present invention, there is provided a crystalline form of remdesivir, APO-I, comprising remdesivir and dimethyl sulfoxide, characterized by a PXRD diffractogram comprising peaks, expressed in degrees 2θ (±0.2°), at 4.0°, 17.0° and 20.3°. In a preferred embodiment of the second aspect, the PXRD diffractogram further comprises at least three peaks, expressed in degrees 2θ (±0.2°), selected from the group consisting of: 10.4°, 13.0°, 14.1°, 15.3°, 17.5°, 18.3°, 22.1°, 23.9°, 25.1° and 25.9°. In a further preferred embodiment of the second aspect, the PXRD diffractogram further comprises peaks, expressed in degrees 2θ (±0.2°), at 10.4°, 13.0°, 14.1°, 15.3°, 17.5°, 18.3°, 22.1°, 23.9°, 25.1° and 25.9°. Preferably, the crystalline form of the second aspect of the invention provides a PXRD diffractogram comprising peaks in substantially the same positions (±0.2° 2θ) as those shown in FIG. 1. In a further preferred embodiment of the second aspect, the crystalline form is characterized by a DSC thermogram comprising an endothermic peak with a peak onset at approximately 101° C. and a peak maximum at approximately 103° C. Preferably, the crystalline form of the second aspect is characterized by a DSC thermogram that is substantially the same in appearance as the DSC thermogram provided in FIG. 3. In a further preferred embodiment of the second aspect, the molar ratio of remdesivir to dimethyl sulfoxide in the crystalline form is between approximately 1:0.75 and approximately 1:1.25.

In a third aspect of the present invention, there is provided a process for the preparation of a crystalline form of remdesivir according to the first or second aspects of the invention, the process comprising:
(1) Preparing a solution of remdesivir in dimethyl sulfoxide at a suitable temperature;
(2) Adding an organic anti-solvent to the solution to form a mixture;
(3) Cooling the mixture, if necessary, to form a suspension comprising remdesivir crystalline form containing dimethyl sulfoxide; and
(4) Isolating the remdesivir crystals from the suspension.

Preferably, in the third aspect of the present invention, there is provided a process for the preparation of a crystalline form of remdesivir according to the second aspect of the invention.

In a preferred embodiment of the third aspect, preparing a solution of remdesivir comprises dissolving remdesivir in dimethyl sulfoxide, preferably at a temperature between approximately 60° C. and approximately 80° C. In a further preferred embodiment of the third aspect, the organic anti-solvent is an ether, preferably a cyclic or acyclic alkyl ether. More preferably, the organic anti-solvent is an acyclic dialkyl ether wherein each alkyl portion has 1 to 5 carbon atoms. Most preferably the organic anti-solvent is methyl tert-butyl ether. In another preferred embodiment of the third aspect, the molar ratio of remdesivir to dimethyl sulfoxide in the crystalline form prepared is between approximately 1:0.75 and approximately 1:1.25. Most preferably, the molar ratio of remdesivir to dimethyl sulfoxide in the crystalline form is approximately 1:1.

In a fourth aspect of the present invention, there is provided a pharmaceutical composition comprising a crystalline form of remdesivir according to the first or second aspects of the invention, or remdesivir prepared according to the process of the third aspect of the invention, and one or more pharmaceutically acceptable excipients. Preferably, the pharmaceutical composition is a lyophilized composition or a solution composition. Most preferably, the pharmaceutical composition is a powder for concentrate for solution for infusion or a concentrate for solution for infusion. Preferably, the pharmaceutical composition of the fourth aspect comprises an amount of the crystalline form of remdesivir of the first or second aspects that is equivalent to 100 mg remdesivir.

In a fifth aspect of the present invention, there is provided the use of a crystalline form of remdesivir according to the first or second aspects of the invention, the remdesivir prepared according to the process of the third aspect of the invention, or the pharmaceutical compositions of the fourth aspect of the invention, in the treatment of a viral infection. In a preferred embodiment of the fifth aspect, the viral infection is caused by a virus selected from the group consisting of an Arenaviridae virus, a Coronaviridae virus, a Filoviridae virus, a Flaviviridae virus, and a Paramyxoviridae virus. In a further preferred embodiment of the fifth aspect, the viral infection is caused by a virus selected from the group consisting of Lassa virus, Junin virus, Severe Acute Respiratory Syndrome coronavirus (SARS-CoV), Severe Acute Respiratory Syndrome coronavirus 2 (SARS-CoV-2), Middle Eastern Respiratory Syndrome coronavirus (MERS-CoV), Ebola virus, Marburg virus, Zika virus, and Respiratory Syncytial virus (RSV). In a more preferred embodiment of the fifth aspect, the viral infection is caused by Severe Acute Respiratory Syndrome coronavirus 2 (SARS-CoV-2).

Non-limiting examples, aspects or embodiments of the present invention will now be described in the following numbered clauses:

Clause 1: A crystalline form of remdesivir comprising remdesivir and dimethyl sulfoxide.

Clause 2. The crystalline form of clause 1, wherein the molar ratio of remdesivir to dimethyl sulfoxide ranges from approximately 1:0.75 to approximately 1:1.25.

Clause 3. The crystalline form of clause 1, wherein the molar ratio of remdesivir to dimethyl sulfoxide is approximately 1:1.

Clause 4. A crystalline form of remdesivir comprising remdesivir and dimethyl sulfoxide characterized by a PXRD diffractogram comprising peaks, expressed in degrees 2θ (±0.2°), at 4.0°, 17.0° and 20.3°.

Clause 5. The crystalline form of clause 4, further comprising at least three peaks in the PXRD diffractogram, expressed in degrees 2θ (±0.2°), selected from the group consisting of: 10.4°, 13.0°, 14.1°, 15.3°, 17.5°, 18.3°, 22.1°, 23.9°, 25.1° and 25.9°.

Clause 6. The crystalline form of clause 4, further comprising peaks in the PXRD diffractogram, expressed in degrees 2θ (±0.2°), at 10.4°, 13.0°, 14.1°, 15.3°, 17.5°, 18.3°, 22.1°, 23.9°, 25.1° and 25.9°.

Clause 7. The crystalline form of any one of clauses 4 to 6 providing a PXRD diffractogram comprising peaks in substantially the same positions (±0.2° 2θ) as those shown in FIG. 1.

Clause 8. The crystalline form of any one of clauses 4 to 7, characterized by a DSC thermogram comprising an endothermic peak with a peak onset at approximately 101° C. and a peak maximum at approximately 103° C.

Clause 9. The crystalline form of any one of clauses 4 to 8, characterized by a DSC thermogram that is substantially the same in appearance as the DSC thermogram provided in FIG. 3.

Clause 10. The crystalline form of any one of clauses 4 to 9, wherein the molar ratio of remdesivir to dimethyl sulfoxide ranges from approximately 1:0.75 to approximately 1:1.25.

Clause 11. The crystalline form of clause 10, wherein the molar ratio of remdesivir to dimethyl sulfoxide is approximately 1:1.

Clause 12. A process for the preparation of the crystalline form of remdesivir of any one of clauses 4 to 11, the process comprising: (1) Preparing a solution of remdesivir in dimethyl sulfoxide at a suitable temperature; (2) Adding an organic anti-solvent to the solution to form a mixture; (3) Cooling the mixture, if necessary, to form a suspension comprising remdesivir crystals containing dimethyl sulfoxide; and (4) Isolating the remdesivir crystals from the suspension.

Clause 13. The process of clause 12, wherein the suitable temperature ranges from approximately 60° C. to approximately 80° C.

Clause 14. The process of clause 12 or clause 13, wherein the organic anti-solvent is a cyclic or acyclic alkyl ether.

Clause 15. The process of clause 14, wherein the organic anti-solvent is methyl t-butyl ether.

Clause 16. A pharmaceutical composition comprising the crystalline form of remdesivir according to any one of clauses 1 to 11, and one or more pharmaceutically acceptable excipients.

Clause 17. The pharmaceutical composition of clause 16, wherein the pharmaceutical composition is a lyophilized composition or a solution composition.

Clause 18. The use of the crystalline form of remdesivir according to any one of clauses 1 to 11 in the treatment of a viral infection.

Clause 19. The use of clause 18, wherein the viral infection is caused by a virus selected from the group consisting of an Arenaviridae virus, a Coronaviridae virus, a Filoviridae virus, a Flaviviridae virus, and a Paramyxoviridae virus.

Clause 20. The use of clause 18, wherein the viral infection is caused by a virus selected from the group consisting of Lassa virus, Junin virus, Severe Acute Respiratory Syndrome coronavirus (SARS-CoV), Severe Acute Respiratory Syndrome coronavirus 2 (SARS-CoV-2), Middle Eastern Respiratory Syndrome coronavirus (MERS-CoV), Ebola virus, Marburg virus, Zika virus, and Respiratory Syncytial virus (RSV).

Clause 21. The use of clause 20, wherein the viral infection is caused by Severe Acute Respiratory Syndrome coronavirus 2 (SARS-CoV-2).

Clause 22. A method of treating viral infection comprising administering a therapeutically effective amount of the crystalline form of remdesivir according to any one of clauses 1 to 11 to a patient in need thereof.

Clause 23. The method of clause 22, wherein the viral infection is caused by a virus selected from the group consisting of an Arenaviridae virus, a Coronaviridae virus, a Filoviridae virus, a Flaviviridae virus, and a Paramyxoviridae virus.

Clause 24. The method of clause 22, wherein the viral infection is caused by a virus selected from the group consisting of Lassa virus, Junin virus, Severe Acute Respiratory Syndrome coronavirus (SARS-CoV), Severe Acute Respiratory Syndrome coronavirus 2 (SARS-CoV-2), Middle Eastern Respiratory Syndrome coronavirus (MERS-CoV), Ebola virus, Marburg virus, Zika virus, and Respiratory Syncytial virus (RSV).

Clause 25. The method of clause 24, wherein the viral infection is caused by Severe Acute Respiratory Syndrome coronavirus 2 (SARS-CoV-2).

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DESCRIPTION OF THE INVENTION

The remdesivir crystalline form of the present invention comprises remdesivir that has crystallized with dimethyl sulfoxide. Importantly, with respect to the use of this crystalline form in the preparation of pharmaceutical compositions, dimethyl sulfoxide is included in both the U.S. Food & Drug Administration's (FDA's) Substances Added to Food inventory (formerly Everything Added to Food in the United States (EAFUS)), and the Inactive Ingredient Database (IID). The Substances Added to Food list contains ingredients added directly to food that the FDA has either approved as food additives, or has listed or affirmed as being GRAS (Generally Recognized As Safe). The IID list provides information on inactive ingredients present in FDA-approved drug products. Once an inactive ingredient has appeared in an approved drug product for a particular route of administration, the inactive ingredient is not considered new, and may require a less extensive review the next time it is included in a new drug product. Of relevance, dimethyl sulfoxide appears in the IID list in association with a powder for suspension for injection dosage form that is administered intravenously.

Furthermore, a number of regulated products for medical use comprise dimethyl sulfoxide as a component, either as part of the formulation or as part of the active ingredient itself. For example, RIMSO-50® is an aqueous dimethyl sulfoxide solution for intravesical instillation approved by the U.S. FDA for use in the symptomatic relief of interstitial cystitis. A dimethyl sulfoxide solvate of trametinib is the active ingredient in the U.S. FDA approved drug product MEKINIST®, which is indicated for the treatment of certain types of melanoma.

The remdesivir crystalline form of the present invention exhibits differences in properties when compared to the known crystalline forms of remdesivir. Properties that differ between the invention and known crystalline forms of remdesivir include crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactability, tabletting, handling, flow, and blending.

Further, the present invention provides a crystalline form of remdesivir that can be prepared by an efficient and industrially compatible process. Importantly, in addition to dimethyl sulfoxide, the preparation of the crystalline form of the present invention as exemplified herein uses Class 3 solvents established by the ICH (International Council for Harmonisation of Technical Requirements for Pharmaceuticals for Human Use) as having low toxicity.

Figure 1:
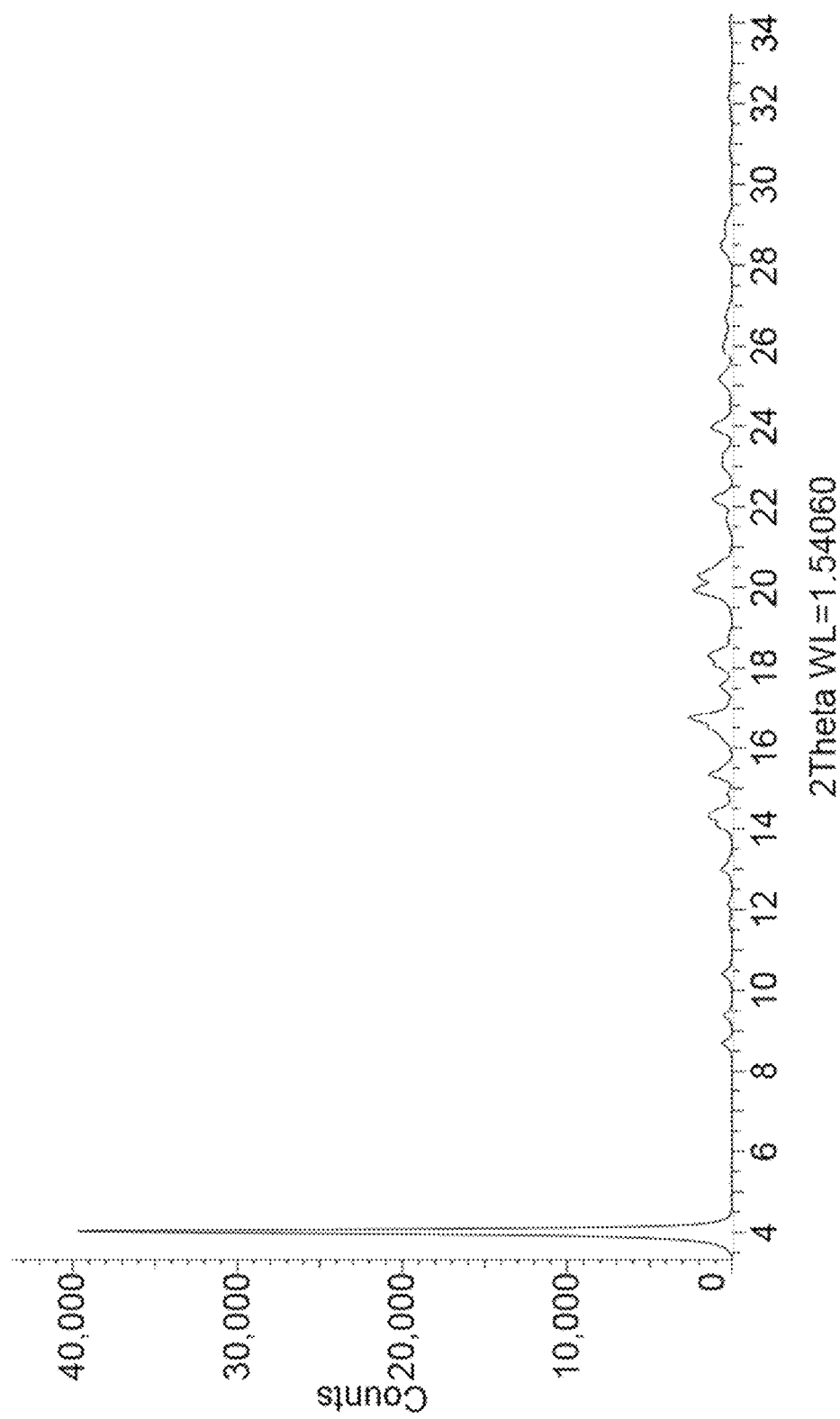
FIG. 1 is a representative PXRD diffractogram of remdesivir Form APO-I as prepared in Example 1.

Depending on the manner in which the crystalline forms of the present invention are prepared, and the methodology and instrument used for PXRD analysis, the intensity of a given peak observed in a PXRD diffractogram of the crystalline form may vary when compared to the same peak in the representative PXRD diffractogram provided in FIG. 1. Thus, differences in relative peak intensities between peaks in a PXRD diffractogram for a given crystalline form may be observed when compared to the relative peak intensities of the peaks in the representative PXRD diffractogram of FIG. 1. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIG. 1, it is understood that individual peak positions may vary between ±0.2° 2θ from the values observed in the representative PXRD diffractograms provided in FIG. 1 for the crystalline form of the invention, or listed in Table 1. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractogram provided in FIG. 1. Thus, PXRD diffractograms of the crystalline form of the present invention may, in some circumstances, display the same relative peak positions as observed in the representative PXRD diffractogram provided in FIG. 1, with the exception that each peak is offset in the same direction, and by approximately the same amount, such that the overall PXRD diffractogram is substantially the same in appearance as the PXRD diffractogram of FIG. 1, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractogram of FIG. 1.

Figure 3:
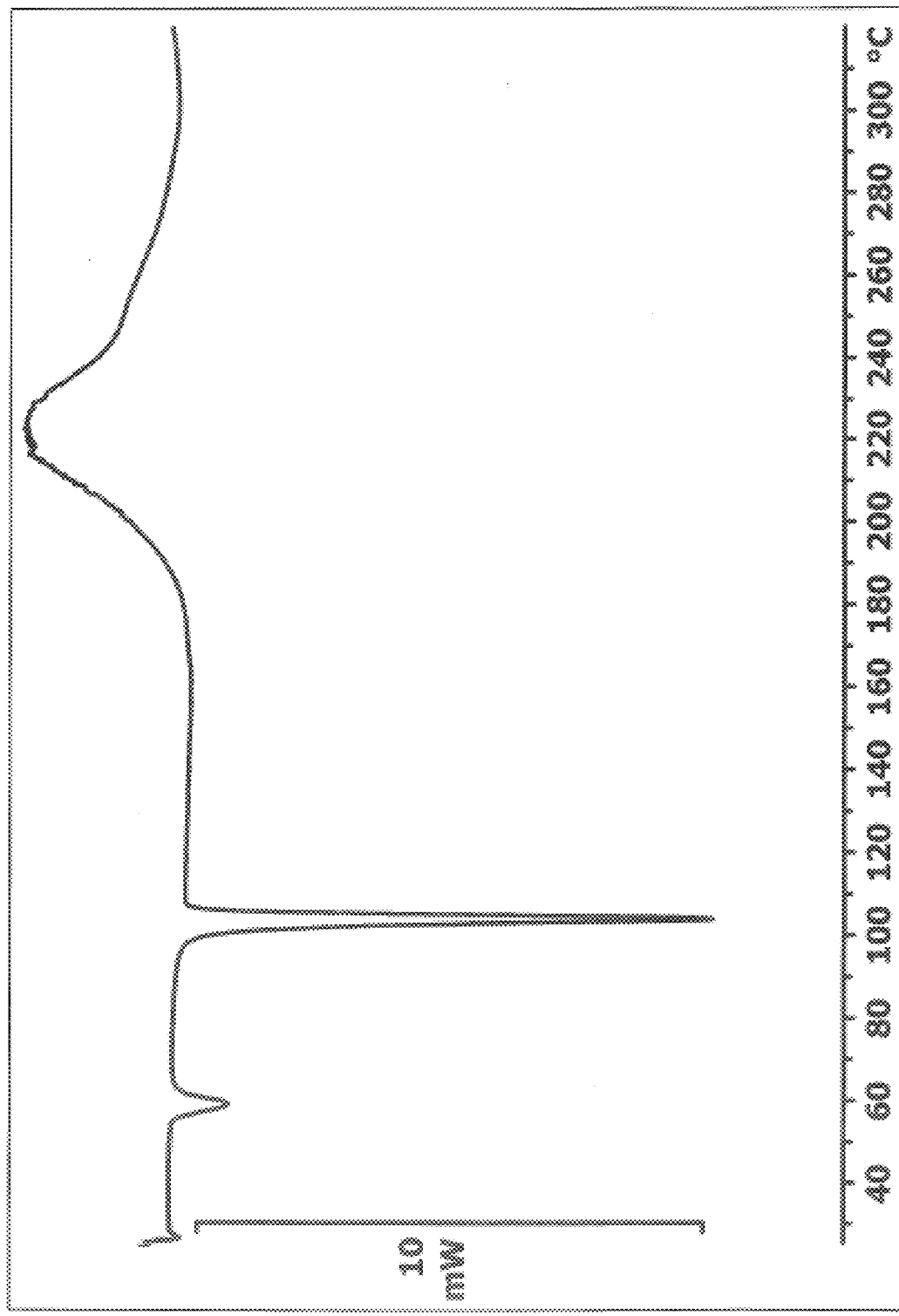
FIG. 3 is a representative DSC thermogram of remdesivir Form APO-I as prepared in Example 1.

Depending on the manner in which the crystalline forms are prepared and the methodology and instrument used for DSC analysis, it is understood that peaks corresponding with thermal events in a DSC thermogram may vary between ±2° C. from the values observed in the representative DSC thermogram provided in FIG. 3 and described herein. Such variations are known and understood by a person of skill in the art, and any such variations do not depart from the invention disclosed herein.

As used herein, the term 'crystalline form' refers to a substance with a particular arrangement of molecular components in its crystal lattice, and which may be identified by physical characterization methods such as PXRD and/or DSC. As used herein, the term crystalline form is intended to include single-component and multiple-component crystalline forms. Single-component forms of remdesivir, such as those known in the art, consist solely of remdesivir in the repeating unit of the crystal lattice. Multiple-component forms of remdesivir, such as those of the present invention, include crystalline forms of remdesivir wherein one or more other molecules are also incorporated into the crystal lattice with remdesivir.

Multi-component crystalline forms comprising more than one type of molecule in the crystalline lattice may have some variability in the exact molar ratio of their components depending on the conditions used for their preparation. For example, a molar ratio of components within a multi-component crystalline form provides a person of skill in the art information as to the general relative quantities of the components of the crystalline form. In many cases, the molar ratio may vary by ±25% from a stated range. With respect to the present invention, a molar ratio of 1:1 should be understood to include the ratios 1:0.75 and 1:1.25, as well as all of the individual ratios in between.

As used herein, the term "room temperature" refers to a temperature in the range of 20° C. to 25° C.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of remdesivir, remdesivir Form APO-I, comprising remdesivir and dimethyl sulfoxide. Preferably, in remdesivir Form APO-I, the molar ratio of remdesivir to dimethyl sulfoxide is approximately 1:1.

Remdesivir Form APO-I can be characterized by a PXRD diffractogram comprising, among other peaks, characteristic peaks, expressed in degrees 2θ (±0.2°), at 4.0°, 17.0° and 20.3°. Preferably, the PXRD diffractogram further comprises at least three peaks, expressed in degrees 2θ (±0.2°), selected from the group consisting of 10.4°, 13.0°, 14.1°, 15.3°, 17.5°, 18.3°, 22.1°, 23.9°, 25.1° and 25.9°. More preferably, the PXRD diffractogram further comprises peaks, expressed in degrees 2θ (±0.2°), at 10.4°, 13.0°, 14.1°, 15.3°, 17.5°, 18.3°, 22.1°, 23.9°, 25.1° and 25.9°. PXRD studies of capped and uncapped samples of remdesivir Form APO-I maintained in a 27° C./60% RH stability chamber for at least 5 weeks showed that no change in the crystalline form occurred.

Figure 2:
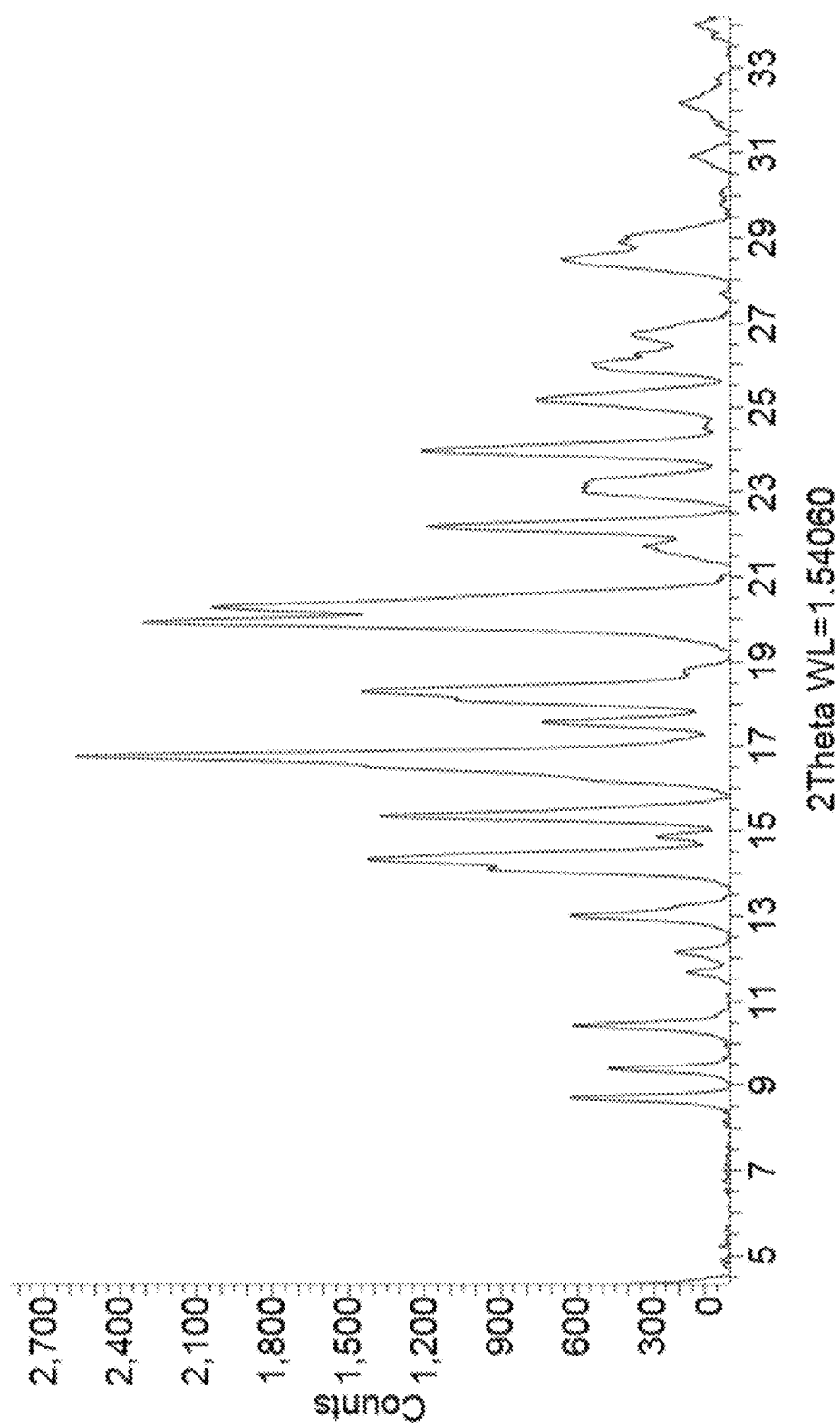
FIG. 2 is a truncated version of FIG. 1 having a condensed 2-theta range.

An illustrative PXRD diffractogram of remdesivir Form APO-I, as prepared in Example 1, is shown in FIG. 1. A truncated version of the PXRD diffractogram shown in FIG. 1 is provided in FIG. 2, wherein the 2-theta scale is adjusted to enlarge the intensity of the higher angle peaks. A peak listing, comprising representative peaks from the PXRD diffractogram in FIG. 1, and their relative intensities, is provided in Table 1. Although illustrative of the PXRD diffractogram that is provided for the remdesivir Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of remdesivir Form APO-I from FIG. 1

| Angle (2θ) | Relative intensity (%) |
|---|---|
| 4.03 | 100.0 |
| 8.68 | 0.4 |
| 9.36 | 0.4 |
| 10.40 | 0.7 |
| 12.11 | 0.3 |
| 13.02 | 0.5 |
| 14.09 | 0.8 |
| 14.30 | 0.7 |
| 15.30 | 1.7 |
| 16.21 | 1.0 |
| 17.00 | 3.5 |
| 17.47 | 0.7 |
| 18.28 | 3.0 |
| 19.88 | 4.2 |
| 20.25 | 5.2 |
| 21.66 | 0.5 |
| 22.11 | 1.2 |
| 23.22 | 0.8 |
| 23.91 | 3.0 |
| 25.13 | 1.4 |
| 25.88 | 1.4 |

An illustrative DSC thermogram of remdesivir Form APO-I is shown in FIG. 3. The DSC thermogram may be further characterized by a first endothermic peak with a peak onset at approximately 55° C. and a peak maximum at approximately 59° C. and a second endothermic peak with a peak onset at approximately 101° C. and a peak maximum at approximately 103° C.

In a further embodiment of the invention, there is provided a process for the preparation of remdesivir Form APO-I, the process comprising:

(1) Preparing a solution of remdesivir in dimethyl sulfoxide at a suitable temperature;
(2) Adding an organic anti-solvent to the solution to form a mixture;
(3) Cooling the mixture, if necessary, to form a suspension comprising remdesivir crystals containing dimethyl sulfoxide; and
(4) Isolating the remdesivir crystals from the suspension.

The step of preparing a solution of remdesivir in dimethyl sulfoxide may involve dissolving the remdesivir in dimethyl sulfoxide or it may involve converting a salt of remdesivir to the free base thereof. Preferably, when remdesivir is used, the suitable temperature for dissolution is elevated, and is preferably between approximately 60° C. and approximately 80° C.

The organic anti-solvent may be an ether, and is preferably a cyclic or acyclic alkyl ether and is selected from the group consisting of diethyl ether, methyl tert-butyl ether, tetrahydrofuran, 2-methyl tetrahydrofuran, and diisopropyl ether. More preferably, the organic anti-solvent is an acrylic dialkyl ether wherein each alkyl portion has 1 to 5 carbon atoms. Most preferably, the organic anti-solvent is methyl tert-butyl ether. The anti-solvent may be added at any suitable temperature, preferably it is added at an elevated temperature between approximately 40° C. and approximately 60° C.

Following addition of the anti-solvent and optional seeding, the resulting suspension can be cooled, preferably to room temperature. Filtration of the suspension, washing and drying in vacuo, preferably at room temperature, affords remdesivir Form APO-I having a PXRD diffractogram and DSC thermogram consistent with FIG. 1 and FIG. 3, respectively.

Figure 4:
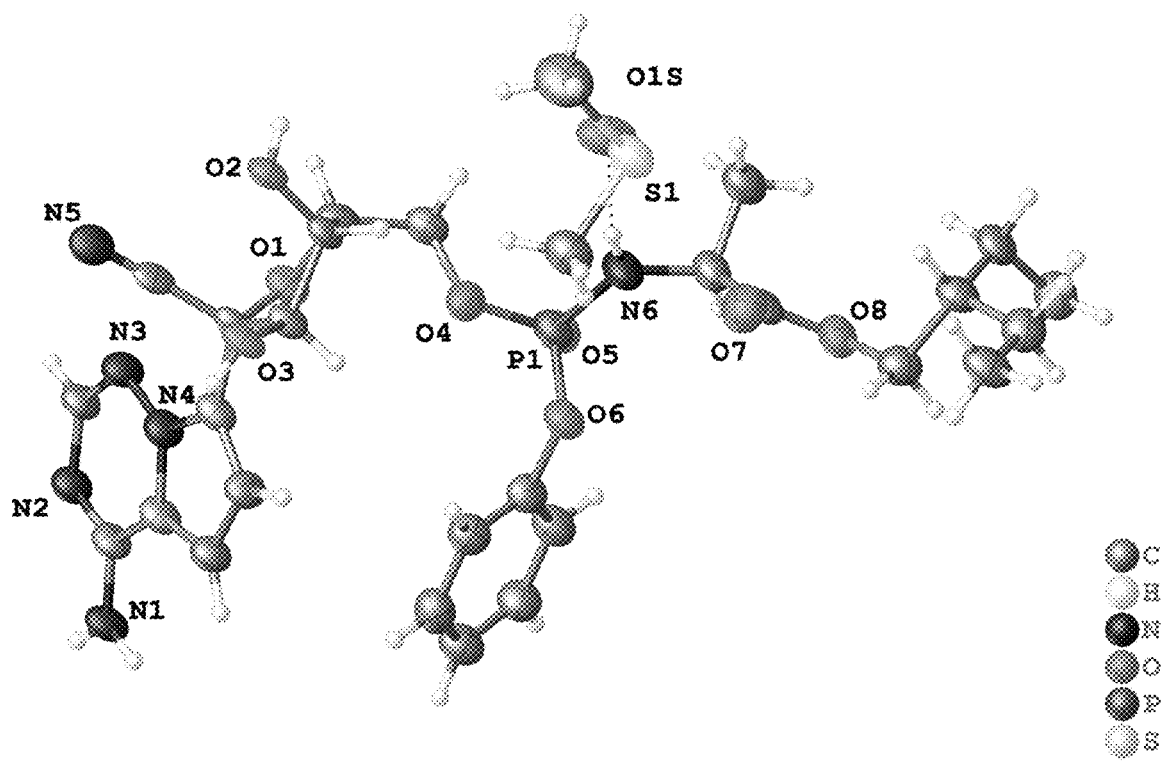
FIG. 4 is an illustration of the SCXRD of remdesivir Form APO-I.

Single crystals of remdesivir Form APO-I were grown from an ethanol/dimethyl sulfoxide solution as described in Example 2 and characterized by SCXRD. A summary of the SCXRD data is provided in Table 2. An illustration of the unit cell from the SCXRD structure is shown in FIG. 4. This illustration depicts a 1:1 remdesivir:dimethyl sulfoxide solvate, i.e., the molar ratio of remdesivir to dimethyl sulfoxide is 1:1.

TABLE 2

Single crystal X-ray diffraction parameters of remdesivir Form APO-I

| Formula | $C_{29}H_{41}N_6O_9PS$ |
|---|---|
| Formula Weight (g/mol) | 680.71 |
| Crystal System | orthorhombic |
| Space Group | $P\ 2_1\ 2_1\ 2_1$ |
| Temperature, K | 110 |
| a, Å | 7.4437(12) |
| b, Å | 10.2884(16) |
| c, Å | 42.856(8) |
| α, ° | 90 |
| β, ° | 90 |
| γ, ° | 90 |
| V, Å$^3$ | 3282.1(10) |
| Z | 4 |
| ρ (g/cm) | 1.378 |
| λ, Å, (CuKα) | 1.54178 |
| Measured fraction of data | 0.958 |
| Unique reflections measured/reflections included in refinement | 7690 |
| $R_1$ | 0.0747 |
| $wR_2$ | 0.1887 |
| $R_1$ (all data) | 0.0929 |
| $wR_2$ (all data) | 0.2027 |
| Goodness of Fit | 1.049 |
| Min & Max peak heights on final ΔF Map (e$^-$/Å) | −0.357, 0.425 |

In a further embodiment of the invention, there is provided a pharmaceutical composition of a crystalline form of remdesivir comprising remdesivir and dimethyl sulfoxide with one or more pharmaceutically acceptable excipients. Preferably, the pharmaceutical composition is a dosage form suitable for parenteral or inhalation administration, such as a lyophilized formulation or a solution formulation. Most preferably, the pharmaceutical composition is a powder for concentrate for solution for infusion or a concentrate for solution for infusion.

As used herein, the phrase "therapeutically effective amount" means that amount of crystalline form of remdesivir (crystalline form of remdesivir comprising remdesivir and dimethyl sulfoxide) that will elicit a biological or medical response of a tissue, system, or patient that is being sought by the administrator (such as a researcher, doctor, or veterinarian) which includes alleviation of the symptoms of the condition or disease being treated and the prevention, slowing or halting of progression of the condition or disease, including but not limited to viral infection. In some examples, the pharmaceutical preparation is in a unit dosage form. In such form, the preparation is subdivided into suitably sized unit doses containing appropriate quantities of the active component, e.g., an effective amount to achieve the desired purpose.

The quantity of crystalline form of remdesivir in a unit dose of preparation comprises or consists of an amount of crystalline form of remdesivir that is equivalent to about 1 mg to about 1000 mg, or about 5 mg to about 500 mg, or about 50 mg to about 250 mg, or about 60 mg to about 240 mg, or about 70 mg to about 230 mg, or about 80 mg to about 220 mg, or about 90 mg to about 210 mg, or about 100 mg to about 200 mg, or about 90 mg to about 110 mg, or about 145 mg to about 165 mg, or about 90 mg to about 175 mg, or about 10 mg, or about 20 mg, or about 30 mg, or about 40 mg, or about 50 mg, or about 60 mg, or about 70 mg, or about 80 mg, or about 90 mg, or about 100 mg, or about 110 mg, or about 120 mg, or about 130 mg, or about 140 mg, or about 150 mg, or about 160 mg, or about 170 mg, or about 180 mg, or about 190 mg, or about 200 mg, or about 210 mg, or about 220 mg, or about 230 mg, or about 240 mg, or about 250 mg, as desired. In some examples, the mixture comprises about 90 mg to about 175 mg, or about 100 mg, or about 150 mg, of remdesivir. For example, an amount of 226 mg of crystalline form of remdesivir provides 200 mg of remdesivir. Similarly, an amount of 113 mg of crystalline form of remdesivir provides 100 mg of remdesivir. The actual dosage employed may be varied depending upon the requirements of the patient and the severity of the condition being treated.

For convenience, the total daily dosage may be divided and administered in portions during the day as required. In some examples, the individual portions can be of the same or different amounts of crystalline form of remdesivir. In some examples, 200 mg of remdesivir (226 mg of crystalline remdesivir) can be administered at day '0' (or sometimes referred to as day '1'), followed by 100 mg/day of remdesivir (113 mg of crystalline remdesivir) to a total of 5 days or a total of 10 days. In some examples, the pharmaceutical composition provides a dose of crystalline form of remdesivir that is equivalent to the 100 mg or 200 mg of remdesivir currently under investigation in clinical trials. Thus, for example, a preferred composition may comprise 113 mg or 226 mg of remdesivir crystalline form providing 100 mg or 200 mg remdesivir, respectively. In some examples, the dosage can range from about 0.001 to about 100 mg/kg of body weight/day of crystalline form of remdesivir, or about 0.01 to about 10 mg/kg of body weight/day. It should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

Suitable pharmaceutically acceptable excipients for use in parenteral compositions are preferably inert with respect to the crystalline form of remdesivir of the present invention, and may include, for example, one or more components selected from vehicles such as water, ethyl alcohol, liquid polyethylene glycol, and propylene glycol; fixed oils such as corn oil, cottonseed oil, peanut oil, and sesame oil; complexing agents such as cyclodextrins and Betadex sulfobutyl ether sodium; surface active agents such as polyoxyethylene sorbitan monolaurate (Tween 20) and polyoxyethylene sorbitan monooleate (Tween 80); tonicity adjusters such as sodium chloride, dextrose, and glycerin; antioxidants such as sodium bisulfite, sulfurous acids, ascorbic acid, and ethylenediaminetetraacetic acid (EDTA); chelating agents; buffers such as citrates, acetates, and phosphates; cryoprotectants and lyoprotectants such as sucrose or trehalose, glycine, lysine, polyethylene glycol, dextran, mannitol, and sorbitol. Other suitable excipients and carriers and the preparation of dosage forms is well known to person of skill in the art, and is described generally, for example, in *Remington The Science and Practice of Pharmacy* 21$^{st}$ Edition (Lippincott Williams & Wilkins: Philadelphia; 2006; Chapter 41).

Alternatively, the remdesivir crystalline forms of the present invention may be formulated as an inhalable composition as described in, for example, WO 2012/012776 A1, which is hereby incorporated by reference.

EXAMPLES

The following non-limiting examples are illustrative of some of the aspects and embodiments of the invention described herein.

The remdesivir used as a starting material in the following example was consistent with Form IV remdesivir which is reported in WO 2018/204198 A1. However, other polymorphic forms are equally suitable as starting material, provided dissolution of the form occurs when preparing the novel crystalline form of remdesivir of the present invention.

PXRD Analysis:

The PXRD diffractogram was recorded on a Bruker D8 Discover powder X-ray diffractometer (Bruker-AXS, Karlsruhe, Germany). The generator was a Micro-focus X-ray source (Incoatec IµS Cu anode, $\lambda=1.54060$ Å) with a voltage of 50 kV and current of 1.00 mA. X-rays were focused with a micro mask 0.1 mm plug-in microslit. One frame was collected using a still scan with a PILATUS3 R 100K-A detector at the distance of 154.72 mm from the sample. Raw data was evaluated using the program EVA (Bruker-AXS, Karlsruhe, Germany).

Differential Scanning Calorimetry Analysis:

The DSC thermogram was collected on a Mettler-Toledo 821e instrument. The sample (2.5018 mg) was weighed into a 40 µL aluminum pan and was crimped closed with an aluminum lid having a 50 µm perforation. The sample was analyzed under a flow of nitrogen (50±5 mL/min) at a scan rate of 10° C./minute between 25° C. and 320° C.

Single Crystal Data Collection and Processing

The sample for SCXRD analysis was mounted on a Mitegen polyimide micromount with a small amount of Paratone N oil. All X-ray measurements were made on a Bruker-Nonius KappaCCD Apex2 diffractometer at a temperature of 110 K. From the initial indexing it was evident that the sample crystal was non-merohedrally twinned (vide infra). The crystal was a not a strong diffractor which limited the amount of data. There was little observable data better than 0.96 Å resolution. The unit cell dimensions were determined from a symmetry constrained fit of 8049 reflections with $8.26°<2\theta<106.02°$. The data collection strategy was a number of ω and φ scans which collected data up to 106.984° (2θ). The frame integration was performed using SAINT (Bruker-AXS, SAINT Version 2013.8, 2013). The resulting raw data was scaled and absorption corrected using a multi-scan averaging of symmetry equivalent data using SADABS (Bruker-AXS, SADABS Version 2012.1, 2012).

Single Crystal Structure Solution and Refinement

The crystal structure was solved by using a dual space methodology with the SHELXT program (Sheldrick, G. M., *Acta Cryst.* 2015, A71, 3-8). All non-hydrogen atoms were obtained from the initial solution, with hydrogen atoms (except the hydrogen bound to N6) being introduced at idealized positions and allowed to ride on the parent atom. The position of the hydrogen atom bound to N6 was obtained from difference Fourier map and was allowed to refine isotropically. The twin fraction was refined and converged to a value of 0.216(2). The asymmetric unit also contained one molecule of DMSO which was disordered over two orientations. The occupancy of the major orientation refined to a value of 0.524(10). The absolute structure was able to be unambiguously determined. The Flack parameter was calculated to be 0.02(3) using Parson quotients (Parsons, S.; Flack, H. D. and Wagner, T. *Acta Cryst.* 2013, B69, 249-259). The structural model was fit to the data using full matrix least-squares based on $F^2$. The calculated structure factors included corrections for anomalous dispersion from the usual tabulation. The structure was refined using the SHELXL program from the SHELX suite of crystallographic software (Sheldrick, G. M., *Acta Cryst.* 2015, C71, 3-8). Graphic plots were produced using the Mercury program suite (Macrae, C. F.; Bruno, I. J.; Chisholm, J. A.; Edington, P. R.; McCabe, P.; Pidcock, E.; Rodriguez-Monge, L.; Taylor, R.; van de Streek, J. and Wood, P. A. *J. Appl. Cryst.*, 2008, 41, 466-470).

Example 1: Preparation of Remdesivir Form APO-I

A suspension of remdesivir (53 mg) in dimethyl sulfoxide (60 µL) was heated to 70° C. Once all solids dissolved, the temperature was adjusted to 50° C. and methyl tert-butyl ether (3.5 mL) was added all at once with vigorous stirring. The cloudy suspension was maintained at 50° C. for one hour, and then allowed to cool to room temperature over approximately 1.5 hours. The precipitated solid was collected by vacuum filtration, washed with methyl tert-butyl ether (2×2 mL) and dried in vacuo at room temperature for 18 hours to afford remdesivir Form APO-I as a white solid (54 mg). $^1$H NMR analysis of the solid (CDCl$_3$, 400 MHz) indicated a molar ratio of remdesivir:DMSO of approximately 1:1. The PXRD diffractogram and DSC thermogram of a sample prepared by this method are shown in FIG. 1 and FIG. 3, respectively.

$^1$H NMR (CDCl$_3$, 400 MHz): δ 8.01 (s, 1H), 7.13-7.18 (m, 2H), 6.99-7.08 (m, 3H), 6.88 (d, J=4.6 Hz, 1H), 6.63 (d, J=4.6 Hz, 1H), 5.83 (br s, 1H), 5.97 (br s, 2H), 4.59-4.64 (m, 1H), 4.21-4.37 (m, 4H), 4.06 (dd, J=10.9, 6.0 Hz, 1H), 3.99 (dd, J=10.9, 5.7 Hz, 1H), 3.89-3.96 (m, 1H), 3.59 (br t, 1H), 3.41 (br s, 1H), 2.62 (s, 6H-DMSO), 1.51 (sep, J=6.2 Hz, 1H), 1.28-1.37 (m, 7H), 0.88 (t, J=7.4 Hz, 6H).

Example 2: Preparation of Single Crystals of Remdesivir Form APO-I

A solution of remdesivir Form APO-I (15 mg) in a mixture (1:0.5) of ethanol/dimethyl sulfoxide (1 mL) was left undisturbed in a loosely capped vial for several months. The resulting plate-shaped crystals were collected after gently decanting the solvent, with one crystal being selected for SCXRD analysis. FIG. 4 depicts an illustration of the SCXRD of the Form APO-I crystals prepared by this method. A single position of the disordered DMSO molecule is shown. PXRD of a portion of the crystals was consistent with that shown in FIG. 1.

Example 3: Preparation of Remdesivir Form APO-I

A suspension of remdesivir (200 mg) in dimethyl sulfoxide (200 µL) was heated to 70° C. Once all solids dissolved, the temperature was adjusted to 50° C. and methyl tert-butyl ether (10.5 mL) was added all at once with vigorous stirring. The suspension was then allowed to cool to room temperature over approximately 1.5 hours. The precipitated solid was collected by vacuum filtration, washed with methyl tert-butyl ether (2×1 mL) and dried in vacuo at room temperature for 18 hours to afford remdesivir Form APO-I as a white solid (211 mg). The PXRD diffractogram of a sample prepared by this method was consistent with that shown in FIG. 1.

Example 4: Comparative Intrinsic Dissolution Testing

Intrinsic dissolution rate (IDR) measurements were performed using a Wood's apparatus. Samples were prepared by compressing an amount (267 mg Form II; 258 mg APO-I) of sample at 1.5 metric tons for 1 minute. A dissolution medium consisting of 900 mL distilled water maintained at 37° C., and rotation speed of 50 rpm, was used for each experiment. Results are provided in Table 3.

TABLE 3

Comparative intrinsic dissolution rates for the crystalline form of the invention with crystalline form II of remdesivir described in WO 2018/204198 A1

| Form | Intrinsic Dissolution Rate (mg min$^{-1}$ cm$^{-2}$) |
| --- | --- |
| Remdesivir Form II (Prior Art) | 0.0083 |
| Remdesivir Form APO-I | 0.013 |

What is claimed is:

1. A crystalline form of remdesivir comprising remdesivir and dimethyl sulfoxide.

2. The crystalline form of claim 1, wherein the molar ratio of remdesivir to dimethyl sulfoxide ranges from approximately 1:0.75 to approximately 1:1.25.

3. The crystalline form of claim 1, wherein the molar ratio of remdesivir to dimethyl sulfoxide is approximately 1:1.

4. A crystalline form of remdesivir comprising remdesivir and dimethyl sulfoxide characterized by a PXRD diffractogram comprising peaks, expressed in degrees 2θ (±0.2°), at 4.0°, 17.0° and 20.3°.

5. The crystalline form of claim 4, further comprising at least three peaks in the PXRD diffractogram, expressed in degrees 2θ (±0.2°), selected from the group consisting of: 10.4°, 13.0°, 14.1°, 15.3°, 17.5°, 18.3°, 22.1°, 23.9°, 25.1° and 25.9°.

6. The crystalline form of claim 4, further comprising peaks in the PXRD diffractogram, expressed in degrees 2θ (±0.2°), at 10.4°, 13.0°, 14.1°, 15.3°, 17.5°, 18.3°, 22.1°, 23.9°, 25.1° and 25.9°.

7. The crystalline form of claim 6, providing a PXRD diffractogram comprising peaks in substantially the same positions (±0.2° 2θ) as those shown in FIG. 1.

8. The crystalline form of claim 4, characterized by a DSC thermogram comprising an endothermic peak with a peak onset at approximately 101° C. and a peak maximum at approximately 103° C.

9. The crystalline form of claim 8, characterized by a DSC thermogram that is substantially the same in appearance as the DSC thermogram provided in FIG. 3.

10. The crystalline form of claim 4, wherein the molar ratio of remdesivir to dimethyl sulfoxide ranges from approximately 1:0.75 to approximately 1:1.25.

11. The crystalline form of claim 10, wherein the molar ratio of remdesivir to dimethyl sulfoxide is approximately 1:1.

12. A process for the preparation of the crystalline form of remdesivir of claim 4, the process comprising:
preparing a solution of remdesivir in dimethyl sulfoxide at a suitable temperature;
adding an organic anti-solvent to the solution to form a mixture;
cooling the mixture, if necessary, to form a suspension comprising remdesivir crystals containing dimethyl sulfoxide; and
isolating the remdesivir crystals from the suspension.

13. The process of claim 12, wherein the suitable temperature ranges from approximately 60° C. to approximately 80° C.

14. The process of claim 13, wherein the organic anti-solvent is a cyclic or acyclic alkyl ether.

15. The process of claim 14, wherein the organic anti-solvent is methyl t-butyl ether.

16. A pharmaceutical composition comprising the crystalline form of remdesivir according to claim 4, and one or more pharmaceutically acceptable excipients.

17. The pharmaceutical composition of claim 16, wherein the pharmaceutical composition is a lyophilized composition or a solution composition.

18. A method of treating viral infection comprising administering a therapeutically effective amount of the crystalline form of remdesivir according to claim 4 to a patient in need thereof.

19. The method of claim 18, wherein the viral infection is caused by a virus selected from the group consisting of an Arenaviridae virus, a Coronaviridae virus, a Filoviridae virus, a Flaviviridae virus, and a Paramyxoviridae virus.

20. The method of claim 18, wherein the viral infection is caused by a virus selected from the group consisting of Lassa virus, Junin virus, Severe Acute Respiratory Syndrome coronavirus (SARS-CoV), Severe Acute Respiratory Syndrome coronavirus 2 (SARS-CoV-2), Middle Eastern Respiratory Syndrome coronavirus (MERS-CoV), Ebola virus, Marburg virus, Zika virus, and Respiratory Syncytial virus (RSV).

21. The method of claim 20, wherein the viral infection is caused by Severe Acute Respiratory Syndrome coronavirus 2 (SARS-CoV-2).

* * * * *